United States Patent
Sakai et al.

(10) Patent No.: US 9,372,161 B2
(45) Date of Patent: Jun. 21, 2016

(54) ION SOURCE, ION GUN, AND ANALYSIS INSTRUMENT

(71) Applicant: ULVAC-PHI, Inc., Chigasaki-shi (JP)

(72) Inventors: Daisuke Sakai, Chigasaki (JP); Mauo Sogou, Chigasaki (JP); Kenzo Hiraoka, Kofu (JP)

(73) Assignee: ULVAC-PHI, INC., Chigasaki-shi (JP)

( * ) Notice: Subject to any disclaimer, the term of this patent is extended or adjusted under 35 U.S.C. 154(b) by 0 days.

(21) Appl. No.: 14/600,338

(22) Filed: Jan. 20, 2015

(65) Prior Publication Data

US 2015/0206732 A1 Jul. 23, 2015

(30) Foreign Application Priority Data

Jan. 22, 2014 (JP) ................................ 2014-009699

(51) Int. Cl.

| | |
|---|---|
| *G01N 23/02* | (2006.01) |
| *H01J 49/26* | (2006.01) |
| *H01J 37/08* | (2006.01) |
| *H01J 37/252* | (2006.01) |
| *H01J 27/26* | (2006.01) |

(Continued)

(52) U.S. Cl.
CPC ................. *G01N 23/02* (2013.01); *H01J 27/26* (2013.01); *H01J 37/08* (2013.01); *H01J 37/252* (2013.01); *H01J 49/0468* (2013.01); *H01J 49/165* (2013.01); *G01N 23/2258* (2013.01); *H01J 2237/0812* (2013.01); *H01J 2237/2527* (2013.01); *H01J 2237/3174* (2013.01)

(58) Field of Classification Search
USPC ............... 250/423 R, 424, 425, 423 P, 423 F; 315/111.01, 111.11, 111.31, 111.41, 315/111.61, 111.81

See application file for complete search history.

(56) References Cited

U.S. PATENT DOCUMENTS

| | | | |
|---|---|---|---|
| 4,160,161 A | 7/1979 | Horton | |
| 5,164,592 A * | 11/1992 | Kitamori | H01J 49/164 250/281 |

(Continued)

FOREIGN PATENT DOCUMENTS

| | | |
|---|---|---|
| EP | 1193730 A1 | 4/2002 |
| JP | H04-354865 | 12/1992 |

(Continued)

OTHER PUBLICATIONS

Extended European search report issued on Jun. 30, 2015 for the European counterpart application No. 15152080.6.

(Continued)

*Primary Examiner* — Nicole Ippolito

(74) *Attorney, Agent, or Firm* — Kratz, Quintos & Hanson, LLP

(57) ABSTRACT

Provided are an ion source, an ion gun, and an analysis instrument, which are capable of performing sputtering without damage to a surface of a sample and improving detection sensitivity in mass spectroscopy. In the ion source, an emission opening to which ionization liquid is supplied is disposed in an electric field formed in vacuum environment by an extracting electrode so that super large droplet cluster ions are generated from the emission opening. When the sample is irradiated with a super large droplet cluster ion beam, the sample surface is subjected to sputtering without damage, so as to remove contamination substances or to expose a new surface of the sample. In mass spectroscopy, detection sensitivity is improved.

11 Claims, 13 Drawing Sheets

(51) Int. Cl.
*H01J 49/04* (2006.01)
*H01J 49/16* (2006.01)
*G01N 23/225* (2006.01)

(56) References Cited

U.S. PATENT DOCUMENTS

2003/0034450 A1 2/2003 Karger et al.
2014/0363678 A1* 12/2014 Kirkpatrick et al. .......... 428/408

FOREIGN PATENT DOCUMENTS

| JP | 2005-134170 A1 | 5/2005 |
| JP | 2008-116363 A1 | 5/2008 |
| JP | 2011-141199 A1 | 7/2011 |
| WO | 8908972 A1 | 9/1989 |

OTHER PUBLICATIONS

Z. Postawa, et. al.; "Microscopic Insights into the Sputtering of Ag{111} Induced by C60 and Ga Bombardment;" J. Phys. Chem. B; vol. 108; No. 23; 2004; pp. 7831-7838 (8 Sheets)/p. 2-3 of specification.

R. Hill, et al.; "The development of C60 and gold cluster ion guns for static SIMS analysis;" Applied Surface Science; 231-232; 2004; pp. 936-939 (4 Sheets)/p. 3 of specification.

S. Rabbani, et. al,: "TOF-SIMS with Argon Gas Cluster Ion Beams. A Comparison with C60;" Analytical Chemistry; vol. 83; 2011; pp. 3793-3800 (8 Sheets)/p. 3 of specification.

* cited by examiner

ION SOURCE, ION GUN, AND ANALYSIS INSTRUMENT

BACKGROUND OF THE INVENTION

1. Field of the Invention

The present invention relates to a technology for realizing low damage sputtering regardless of materials (such as, an inorganic or organic material) in a surface analysis method, and relates to a technology for realizing improvement of sensitivity by improving secondary ion yield in a secondary ion mass spectroscopy method.

2. Description of the Related Art

An ion source for surface analysis that can perform sputtering without any damage to a target sample has not yet been developed. In the surface analysis, argon ion ($Ar^+$) is the most common ion species for sputtering, but it is known that the occurrence of damage due to the sputtering is high.

In addition, in a secondary ion mass spectroscopy method (SIMS) as one of surface analysis methods, a primary ion beam that has been used so far is a noble gas ion or a metal ion ($Cs^+$, $Ar^+$, $Ga^+$, $Au^+$, or the like). Some of them can be reduced to a small beam in the order of several tens nanometer, but the occurrence of large damage to a sample is a common drawback.

In addition, if these ions are used as a primary ion source, secondary ion yield is very low, and secondary ion generation efficiency is low. Therefore, in order to overcome the drawback of the SIMS using them as the primary beam, a cluster ion SIMS has been developed. A beam source thereof is $Au_3^{++}$, $Bi_3^{++}$, or the like. By using the cluster ion ($Au_3^{++}$, $Bi_3^{++}$, or the like) consisting several atoms, desorption efficiency of the secondary ions is significantly increased in a non-linear manner. Such result is due to the generation of ablation.

On the other hand, because a target sample surface and its vicinity are significantly damaged, application of the conventional system to a biological material is difficult; and nondestructive observation of molecule ions is difficult; specifically, the sample receives large fragmentation, and a surface of the sample is decomposed and polymerized.

A cluster ion source of $C_{60}^+$ ion is commercialized; and hence, a low damage sputtering technology is realized though in a limited manner. Further, the desorption efficiency is further increased in the SIMS using the $C_{60}^+$ ion source as the primary ion source. However, the following phenomena are caused: (1) an inorganic material is contaminated with a carbon component derived from $C_{60}$; (2) craters are generated in a surface of the material so that surface destruction occurs; (3) a biological sample or the like is significantly damaged; and (4) the secondary ion yield is low in the SIMS, and when the beam diameter is decreased, ionic strength is weakened so that utility value as the SIMS is deteriorated (particularly in an organic material). Refer to Japanese Patent Application Laid-open No. 2005-134170, Journal of Physical Chemistry B, 108, pp 7831-7838, and Applied Surface Science 231-232, pp 936-939, FIG. 4.

There is a surface analysis method utilizing a gas cluster ion beam (GCIB) that has been recently popular, in which noble gas (such as argon (Ar)) is ejected in vacuum to form a jet stream, gas temperature is decreased, and neutral clusters having an n value of $Ar_n^+$ of a few thousands to a few tens of thousands are formed and ionized to generate $Ar_n^+$, which is accelerated to impact the sample.

With this method, depth profile analysis with low-damage sputtering for an organic material (such as a polymer) is confirmed to be effective and is commercialized. However, for an inorganic material (such as a ceramic material) that is relatively hard, the sputtering speed is extremely slow so that it is not practical. Therefore, a range of the sample types to be analyzed is inevitably limited to mainly organic industrial materials.

In addition, when the GCIB is used as the primary ion source in the secondary ion mass spectroscopy method, it is known that the secondary ion yield thereof is low; and hence, it is not practical when used for improving sensitivity in the secondary ion mass spectroscopy method. Refer to Japanese Patent Application Laid-open No. Hei 04-354865, Japanese Patent Application Laid-open No. 2008-116363, and Analytical Chemistry, 2011, 83(10), pp 3793-3800, FIG. 7.

In addition, an ion beam technology using a charged droplet method has been developed. In this method, a capillary is disposed in the atmosphere, solvent is supplied through inside of the capillary, and an extraction electrode that is applied with a high voltage negative with respect to the capillary is disposed in front of the capillary so as to generate ions in the atmosphere.

A vacuum chamber is separated into several steps from low vacuum side to high vacuum side with small diameter orifices. The ions are made to pass through the orifices and are transported to vacuum atmosphere so as to be used as ion beam. In this case, the cluster ions generated in the atmosphere inevitably collide with gas molecules in the atmosphere so that many ions are scattered. Therefore, the amount of ions that are actually transported to the vacuum side and can be effectively used is small; and in addition, downsizing of the cluster ion (fission of the cluster) also occurs due to vaporization in the atmosphere side.

In addition, to use the ion beam, it is necessary to apply a high voltage, which is positive with respect to the ground potential, to the capillary as a source, and it is also necessary to apply a high voltage to parts for lens effect or the like in a low vacuum region during the ion transportation process. Therefore, discharge phenomenon tends to occur in various parts. Consequently, it becomes difficult to stably obtain the ion beam, and it is also difficult to decrease the beam size to be small.

On the other hand, a differential pumping system for evacuating the separated vacuum chamber also becomes large in scale which causes difficulty when in use. Refer to Japanese Patent Application Laid-open No. 2011-141199.

Consequently, a practical ion source that can support various types in etching layer-by-layer without damaging a surface of the sample after irradiation has not been developed yet, and an ion source succeeding in dramatic improvement of sensitivity in the secondary ion mass spectroscopy method has also not yet been developed.

A charged droplet ion source of the related art is described below. In FIG. 5, a charged droplet ion source 701 includes a vacuum chamber 710.

The vacuum chamber 710 is connected to first and second vacuum evacuating devices 729a and 729b so that the inside of the vacuum chamber 710 can be evacuated.

An extracting electrode 721 is provided with a small hole (orifice) so that gas flows in the vacuum chamber 710 through the extracting electrode 721 when the inside of the vacuum chamber 710 is evacuated. First, the inside of the vacuum chamber 710 is evacuated by the first and second vacuum evacuating devices 729a and 729b.

An emission tube (capillary) 703 is disposed outside the vacuum chamber 710.

The distal end of the emission tube 703 is directed towards the small hole of the extracting electrode 721; and a base part thereof on the opposite side is connected to a liquid supply pipe 743. The liquid supply pipe 743 is connected to an ionization liquid supply device 705.

The ionization liquid supply device 705 includes a liquid storing portion 732 and a liquid feeding pump 731. The ionization liquid stored in the liquid storing portion 732 is supplied to the base part of the emission tube 703 through the liquid supply pipe 743 by the liquid feeding pump 731, passes a thin tube in the emission tube 703, and is emitted to the outside of the emission tube 703 from an emission opening 735 at the distal end of the emission tube 703. The emission tube 703 is surrounded by an outer cylinder 707. When carrier gas (here, nitrogen gas) is supplied from a carrier gas source 708 to the inside of the outer cylinder 707, the gas is released from a distal end opening 736 of the outer cylinder 707.

The emission opening 735 is disposed between the distal end opening 736 of the outer cylinder and the small hole of the extracting electrode 721. Around the emission opening 735, there is formed a flow of the carrier gas from an upstream side as the base side of the emission tube 703 to a downstream side on which the extracting electrode 721 is located with the small hole.

An extraction power supply 728 is disposed outside the vacuum chamber 710.

In a state where the carrier gas supplied from the carrier gas source 708 is released from the distal end opening 736, the liquid feeding pump 731 supplies the ionization liquid to the emission opening 735, the extraction power supply 728 applies a voltage between the emission tube 703 (made of a metal here) and the extracting electrode 721 so that an electric field thereof extracts droplet cluster ions charged with a positive charge from the ionization liquid positioned in the emission opening 735. Then, the cluster ions pass through the small hole of the extracting electrode 721 and enter the inside of the vacuum chamber 710.

On the downstream side of the extracting electrode 721, there are disposed accelerating electrodes 722 and 723 with small holes and transport lens electrodes 724 and 725. When voltages are applied to the electrodes 722 to 725, the droplet cluster ions entering the inside of the vacuum chamber 710 pass through holes formed in the electrodes 722 to 725 so as to be a droplet cluster ion beam, and further propagates toward the downstream side.

A size of an initial droplet cluster ion generated in the atmosphere is approximately 100 nm in diameter. However, the droplet cluster ion generated in the atmosphere is downsized due to Rayleigh fission that occurs when Coulomb repulsion of itself exceeds surface tension of the droplet. Further, the droplet cluster ions inevitably collide with gas molecules in the atmosphere so that many ions are scattered. Therefore, only a small amount of the droplet cluster ions can enter the inside of the vacuum chamber 710, and the size of the droplet cluster ion is decreased to be smaller than that of initially generated one.

In addition, for use as the droplet cluster ion beam, it is necessary to apply a positive high voltage with respect to the ground potential to the emission tube 703 as the generation source. Further, it is also necessary to apply high voltages to the extracting electrode 721, the first accelerating electrode 722, and the transport lens electrode 724 disposed in the low vacuum environments in the vacuum chamber 710. Therefore, an arcing phenomenon is apt to occur in the vacuum chamber 710, and hence it is difficult to obtain the droplet cluster ion beam.

In addition, it is necessary to separate the atmosphere outside the vacuum chamber 710 from the inside space of the vacuum chamber 710, both of which are connected to each other through the small hole of the extracting electrode 721.

Therefore, the first and second vacuum evacuating devices 729a and 729b for evacuating the inside space of the vacuum chamber 710 are required to be large ones; and hence, difficulty arises when they are used in that they occupy large areas and in terms of cost.

Consequently, in the ion source on the conventional technology, disposing the emission opening of the emission tube in the atmosphere so that the droplet cluster ion beam is generated in the atmosphere provides small amount of the droplet cluster ions that can be actually used. Hence, the conventional technology is of little practical use.

SUMMARY OF THE INVENTION

It is an object of the present invention to achieve depth profile analysis for various types of samples made of organic and inorganic materials and a composite thereof in various types of surface analysis, while suppressing damage to a acceptable level.

In addition, in the secondary ion mass spectroscopy method, for a sample that has been excluded from object of the analysis because of its low secondary ion yield, the problem is solved by improving the sensitivity in the analysis of the secondary ion mass spectroscopy method.

In order to solve the above-mentioned problem, the present invention is an ion source, including a vacuum chamber; an emission tube inserted in the vacuum chamber in a hermetic manner, the emission tube having conductivity in at least a surface thereof; an ionization liquid supply device disposed outside the vacuum chamber so as to supply ionization liquid to a thin tube disposed in the emission tube, at a part positioned outside the vacuum chamber; an extracting electrode configured to extract ions in the ionization liquid supplied from the ionization liquid supply device to the emission tube, as cluster ions from an emission opening of the thin tube positioned inside the vacuum chamber and to cause the cluster ions to fly in vacuum environment; and a laser beam emitting device configured to irradiate the emission opening with a laser beam.

The present invention is an ion source, wherein a transparent window for observation of the emission opening is provided on the vacuum chamber, and wherein the vacuum chamber is configured to be able to observe the emission opening through the transparent window for observation.

The present invention is an ion source, further including a measurement device disposed outside the vacuum chamber for observing the emission opening and for checking whether or not the emission opening is irradiated with the laser beam.

The present invention is an ion source, further including an optical microscope for observing the emission opening, the optical microscope being disposed outside the vacuum chamber.

The present invention is an ion source, wherein the laser beam emitting device emits the laser beam having a wavelength in a range of from $0.3 \times 10^{-6}$ m to $1 \times 10^{-6}$ m.

The present invention is an ion source, wherein the ionization liquid contains at least one type of solvent selected from the group consisting of water, alcohol, acetonitrile, acetic acid, and trifluoroacetic acid.

The present invention is an ion gun for emitting a cluster ion beam, including a ion source and a focusing device configured to focus and deflect a flow of the flying cluster ions so as to generate the cluster ion beam; the ion source including: a vacuum chamber; an emission tube inserted in the vacuum chamber in a hermetic manner, the emission tube having conductivity in at least a surface thereof; an ionization liquid supply device disposed outside the vacuum chamber so as to supply ionization liquid to a thin tube disposed in the emission tube, at a part positioned outside the vacuum chamber; an extracting electrode configured to extract ions in the ionization liquid supplied from the ionization liquid supply device to the emission tube, as cluster ions from an emission opening of the thin tube positioned inside the vacuum chamber and to cause the cluster ions to fly in vacuum environment; and a laser beam emitting device configured to irradiate the emission opening with a laser beam.

The present invention is an analysis instrument for analyzing a surface of a sample, including: an ion gun for emitting a cluster ion beam; and a sample stage portion on which the sample is placed and the sample is irradiated with the cluster ion beam, the ion gun including: an ion source; and a focusing device configured to focus and deflect a flow of the flying cluster ions so as to generate the cluster ion beam; the ion source including: a vacuum chamber; an emission tube inserted in the vacuum chamber in a hermetic manner, the emission tube having conductivity in at least a surface thereof; an ionization liquid supply device disposed outside the vacuum chamber so as to supply ionization liquid to a thin tube disposed in the emission tube, at a part positioned outside the vacuum chamber; an extracting electrode configured to extract ions in the ionization liquid supplied from the ionization liquid supply device to the emission tube, as cluster ions from an emission opening of the thin tube positioned inside the vacuum chamber and to cause the cluster ions to fly in vacuum environment; and a laser beam emitting device configured to irradiate the emission opening with a laser beam.

The present invention is an analysis instrument, further including: a mass spectrometer configured to pass through secondary ions having an objective mass-to-charge ratio among secondary ions emitted from a part of the sample irradiated with the cluster ions; a detector configured to detect the secondary ions that have passed through the mass spectrometer; and a data processor configured to determine an amount of the secondary ions for each mass of the secondary ions based on a result of detection by the detector.

The present invention is an analysis instrument, further including a metal ion gun configured to irradiate the sample with a primary beam of metal ions.

The present invention is an analysis instrument, further including: an X-ray emitting device configured to emit an X-ray to irradiate the surface of the sample irradiated with the cluster ions; an electron spectrometer configured to pass through electrons having objective energy among electrons emitted from a part of the sample irradiated with the X-ray; and an electron detector configured to detect the electrons that have passed through the electron spectrometer.

According to the present invention, there is provided an ion source including: a vacuum chamber; an emission tube inserted in the vacuum chamber in a hermetic manner, the emission tube having conductivity in at least a surface thereof; an ionization liquid supply device disposed outside the vacuum chamber so as to supply a thin tube disposed in the emission tube at a part positioned outside the vacuum chamber with ionization liquid; an extracting electrode configured to extract ions in the ionization liquid, supplied from the ionization liquid supply device to the emission tube, from an emission opening of the thin tube positioned inside the vacuum chamber as cluster ions and to make the cluster ions fly in vacuum environment; and a laser beam emitting device configured to irradiate the emission opening with a laser beam.

According to the present invention, an ion source, positioned in the vacuum chamber which is equipped with a transparent window, is configured to be able to observe the emission opening through the transparent window for the observation of the emission opening.

According to the present invention, the ion source further comprises a measurement device disposed outside the vacuum chamber for observing the emission opening and checking whether or not the emission opening is irradiated with the laser beam.

According to the present invention, the ion source further includes an optical microscope for observing the emission opening disposed outside the vacuum chamber.

According to the present invention the ion source contains the laser beam emitting device emitting the laser beam having a wavelength in a range of from $0.3 \times 10^{-6}$ m to $1 \times 10^{-6}$ m.

According to the present invention, the ion source includes the ionization liquid made from at least one type of solvent selected from the group consisting of water, alcohol, acetonitrile, acetic acid, and trifluoroacetic acid.

According to the present invention, there is provided an ion gun for emitting a cluster ion beam including: the ion source; and a focusing device configured to focus and deflect a flow of the flying cluster ions so as to form the cluster ion beam.

According to the present invention, there is provided an analysis instrument for analyzing a surface of a sample, including: the ion gun; and a sample stage portion on which the sample is placed and the sample is irradiated with the cluster ion beam.

According to the present invention, the analysis instrument further includes: a mass spectrometer configured to pass through secondary ions having an objective mass-to-charge ratio among secondary ions emitted from a part of the sample irradiated with the cluster ions; a detector configured to detect the secondary ions that have passed through the mass spectrometer; and a data processor configured to determine an amount of the secondary ions for each mass of the secondary ions based on a result of detection by the detector.

According to the present invention, the analysis instrument further includes a metal ion gun configured to irradiate the sample with a primary beam of metal ions.

According to the present invention, the analysis instrument further includes: an X-ray emitting device configured to emit an X-ray to irradiate the surface of the sample irradiated with the cluster ions; an electron spectrometer configured to pass through electrons having objective energy among electrons emitted from a part of the sample irradiated with the X-ray; and an electron detector configured to detect the electrons that have passed through the electron spectrometer.

Because the ions are extracted from the ionization liquid in the vacuum environment, super large droplet cluster ions containing many atoms can be generated.

In this case, because the extracted droplet cluster ions do not collide with molecules in the atmosphere, the generated cluster ions are not broken. Therefore, a super large droplet cluster ion beam can be formed; and hence, application to various types of samples is possible.

In addition, because the portion applied with a high voltage for forming the super large droplet cluster ion beam is disposed inside the vacuum environment, arcing hardly occurs.

BRIEF DESCRIPTION OF THE DRAWINGS

FIG. 1-2 is an enlarged diagram of a distal end portion.
FIG. 2-1 illustrates an example of an ion gun.
FIG. 2-2 illustrates another example of the ion gun.

FIG. 9-1 is a graph showing a concentration variation in the depth profile analysis result for an inorganic ceramic material by the X-ray photoelectron spectroscopy analysis instrument of the present invention.

FIG. 9-2 is a graph showing a superposition of results for a plurality times of the analysis.

FIG. 10-1 is a graph showing a concentration variation in the depth profile result for an inorganic ceramic material by X-ray photoelectron spectroscopy analysis with argon gas cluster ion beam.

FIG. 10-2 is a graph showing a superposition of results for a plurality times of the analysis.

FIG. 11-1 is a graph showing the result of an analysis before irradiating a sample with a cluster ion beam of a TOF-SIMS analysis instrument of the present invention (No. 1).

FIG. 11-2 is a graph showing the result of an analysis after irradiation with the cluster ion beam (No. 1).

FIG. 12-1 is a graph showing the result of an analysis before irradiating the sample with the cluster ion beam of the TOF-SIMS analysis instrument of the present invention (No. 2).

FIG. 12-2 is a graph showing the result of an analysis after irradiation with the cluster ion beam (No. 2).

DETAILED DESCRIPTION OF THE PREFERRED EMBODIMENTS

Figure 1:
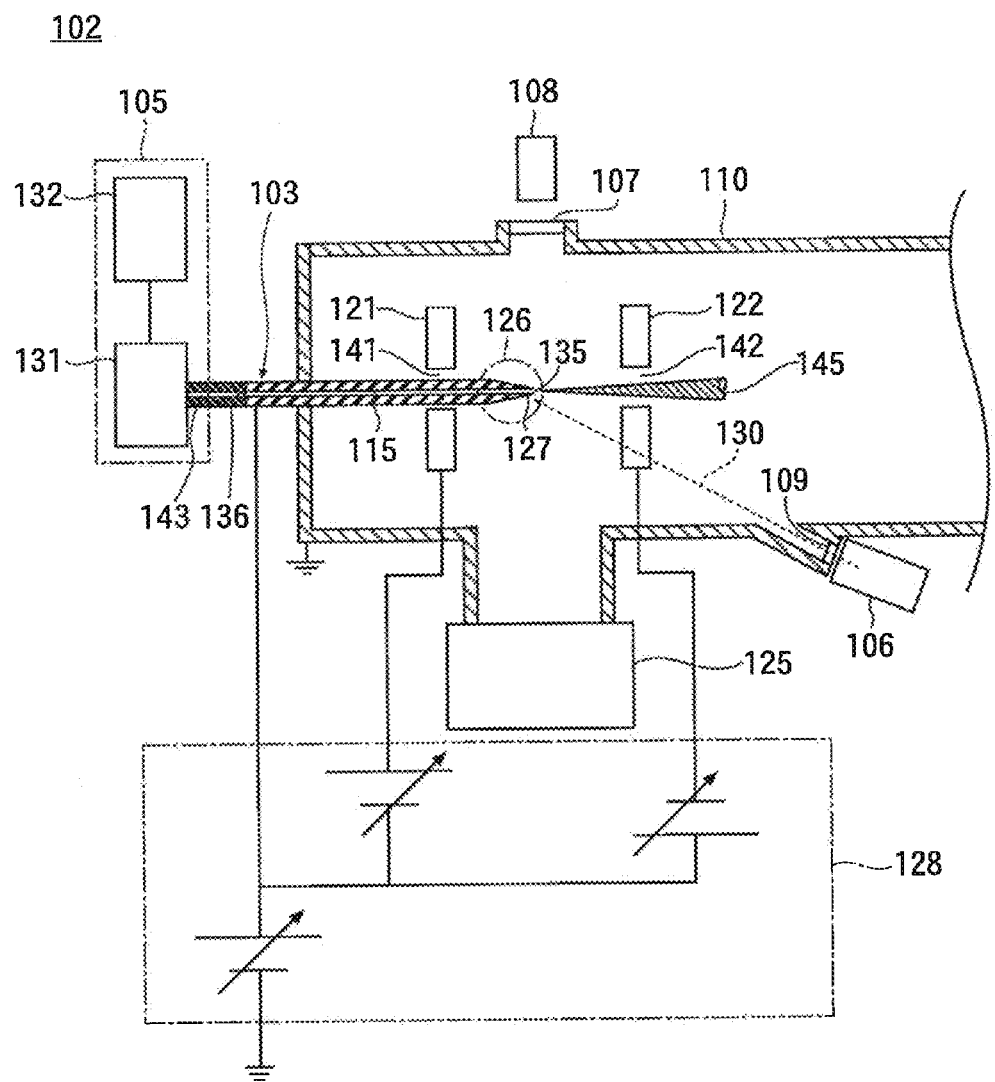
FIG. 1-1 illustrates an example of an ion source.

In order to obtain a droplet cluster ion beam by a charged droplet method, it is necessary to flow ionization liquid for forming ions in a thin tube inside an emission tube (capillary) for generating ions, and to apply an electric field to a distal end of the thin tube, so as to generate droplet cluster ions as an electrospray.

The capillary to be a generation source of ions is disposed in a vacuum; and hence, the electrospray can be stably generated. In order to generate the electrospray, it is necessary to dispose an extracting electrode at a front position of the capillary and to apply a high voltage that is negative with respect to the capillary. Therefore, an emission opening of the capillary for emitting ions is disposed in vacuum environment.

It is preferred that the capillary has a diameter of 0.1 mm or smaller at a small hole for transporting the ionization liquid and an outer diameter of 0.3 mm or smaller. In other words, it is desired to use a material that can be processed to be as thin as possible and to have a thin and smoothly tapered distal end.

It is suitable to use a metal material for forming the capillary.

Examples of the metal material of the capillary include stainless steel, nickel, gold, silver, platinum, copper, aluminum, chromium, titanium, molybdenum, tantalum, niobium, tungsten, and an alloy thereof.

On the other hand, a silica glass capillary is suitable for the material of the capillary due to its distal end being readily sharpened. However, because the silica glass capillary is an insulator, in order to generate a strong electric field in a vicinity of the capillary distal end, it is necessary to dispose a conductive material at the distal end portion and to apply a voltage thereto. Therefore, it is preferred to form the capillary using a conductive material, but it is possible to use an insulator by forming a thin film of a conductive material (such as, gold coating) on the surface of the capillary or by inserting a thin metal wire inside, so as to make the vicinity of the emission opening to be conductive.

Examples of the ionization liquid supplied into the thin tube of the capillary include water, alcohol, acetonitrile, acetic acid, trifluoroacetic acid, or the like, which can be diluted in solvent when used.

As to the ionization liquid for forming ions, it is preferred to contain ionized ions in the ionization liquid because large ion current can be easily obtained by electrospray.

When electrospray (ion emission) is generated by the electric field with the capillary disposed in a vacuum, the ionization liquid is vaporized at the capillary distal end portion, and freezing of the ionization liquid occurs due to evaporative heat loss. When the freezing occurs, the thin tube is blocked so that the ionization liquid cannot be vaporized. In order to stably sustain the electrospray, it is necessary to prevent the freezing.

In order to prevent the freezing, the distal end portion of the capillary is irradiated with a laser beam. When only the capillary distal end portion is irradiated with a sufficiently condensed laser beam, the freezing can be prevented without unnecessarily heating other parts of the capillary. Thus, power consumption for generating the laser beam can be reduced, and deformation of the capillary can be prevented.

In an ion source illustrated in FIGS. 1-1 and 1-2 (discussed later), a wavelength of the laser beam is within a wavelength range from visible light to near infrared light, and the laser beam having a wavelength in the range of 0.3 µm to 1 µm can be used. A laser power of 1 W or smaller is sufficient by focusing the laser beam. It is effective to simultaneously use an optical microscope or the like for observing and confirming an irradiation position of the focused laser beam with high magnification in order to adjust the irradiation position of the laser beam so that a region including the emission opening is irradiated.

When preventing the freezing by the laser beam, the ionization liquid is emitted by the electric field from the emission opening of the capillary disposed in the vacuum. Then, droplet cluster ions are emitted from the emission opening.

Because an ion source for generating super large droplet cluster ions can emit a stable cluster ion beam, it is possible to provide an ion gun with focusing and accelerating functions, consisting of the ion source and an electrostatic lens and deflection system for controlling beam size and direction of the cluster ion beam. This ion gun can be applied to various applications such as surface analysis, sample processing before observation by electron microscope (removal of contamination substances), or the like (FIGS. 2-1 and 2-2).

As examples, discussed below are, for instance, two applications in surface analysis using the ion gun.

A first application is an application that can perform more effective analysis in the depth profile using this ion gun in an X-ray photoelectron spectroscopy (XPS), a secondary ion mass spectroscopy (SIMS), or the like.

Using this ion gun, it is possible to irradiate the sample with the super large droplet cluster ion beam so as to perform low damage sputtering of the sample. Therefore, similar to the argon gas cluster ion beam (Ar-GCIB), this application is effective for analyzing an organic material sample.

Further, this application is also effective for analyzing an inorganic material sample for which Ar-GCIB cannot be used.

Because the emission opening of the capillary is disposed in the vacuum environment, it is possible to generate the ion beam having a larger cluster size than the ion beam that can be generated by the related-art charged droplet ion source having the emission opening disposed in the atmosphere. Therefore, a sample damage ratio can be extremely small.

Further, because the cluster ion beam can have a large beam current and good stability, this application has high utility and efficiency in analysis.

A second application is an application that can improve secondary ion yield and sensitivity in the secondary ion mass spectroscopy method (SIMS).

There are two methods thereof. First, in the measurement of a time-of-flight secondary ion mass spectroscopy method (TOF-SIMS), in addition to a pulse beam type primary ion gun (for example, $Ga^+$, $Au^+$, $Bi^+$, $Au_3^{++}$, or $Bi_3^{++}$) for generating a primary ion beam of the secondary ion mass spectroscopy instrument, there is disposed the ion gun for emitting the super large droplet cluster ion beam to the irradiation position on the sample irradiated with the primary ion beam.

When the irradiation position is irradiated with the primary ion beam so as to analyze emitted secondary ions for sample analysis, the irradiation position is irradiated with the super large droplet cluster ion beam before irradiation with the primary ion beam.

Because the irradiation with the primary ion beam is performed after the irradiation with the super large droplet cluster ion beam, the secondary ion yield is enhanced so that detection sensitivity is increased.

As to the next example, a super large droplet cluster ion gun can be used as the SIMS primary ion gun. When the super large droplet cluster ion source having a sensitivity-increasing effect is used as the primary ion gun, improvement of sensitivity can be expected to be the same as if the SIMS primary ion gun was used.

In the depth profile analysis using the super large droplet cluster ion gun, both the above-described low damage sputtering effect and the detection sensitivity enhancement effect due to increase of the secondary ion yield can be obtained at the same time. Therefore, the depth profile analysis by the secondary ion mass spectroscopy method using the cluster ion gun has significant importance.

The ion beam according to the present invention is superior to existing gas cluster ion beam (GCIB) technologies in that the application range of sample materials with the low damage sputtering for surface analysis is wide.

The GCIB is confirmed to be effective in the sample depth profile analysis for an organic material sample (such as, polymer) because low damage sputtering can be performed. However, the sputtering speed becomes extremely slow for a sample made of an inorganic material (such as a ceramic material, etc.) that is a relatively hard material. Therefore, a range of the sample to be analyzed by the GCIB is inevitably limited to mainly organic industrial materials.

On the other hand, the ion source or the ion beam gun of the present invention has the same performance of low damage sputtering for a sample made of a material to which the GCIB can be applied. In addition, low damage sputtering is realized also for an inorganic material (such as a ceramic material, etc.) sample to which the GCIB cannot be applied. Thus, regardless of an organic or inorganic sample, or a sample made of a composite material thereof, the sample can be analyzed. Therefore, the surface analysis method can also be applied to a sample made of a material that cannot be supported by the existing technology.

On the other hand, the ion source of the present invention hardly causes scattering due to collision between the droplet cluster ion and molecules of atmosphere unlike the related-art atmospheric ion source, and hardly causes downsizing due to rapid decrease of droplet temperature in the vacuum. Therefore, it is possible to form droplet cluster ions having a so-called super large droplet cluster size of approximately 100 nm in diameter. In addition, it is possible to form the droplet cluster ion beam having current of 10 nA or larger.

Because the scattering does not occur, a virtual ion source size is decreased, and the ion beam diameter when irradiating the sample can be decreased to be $\phi50$ μm or smaller. Thus, a cluster ion beam having high intensity can be stably generated.

In addition, in the droplet ion source of the existing technology, accelerating voltage of 7 kV or higher cannot be applied to the emission tube. In contrast, in the present invention, accelerating voltage of 17.5 kV or higher can be applied to the emission tube.

In addition, in the present invention, a flow rate of the introduced ionization liquid is several μL/min or smaller. This is converted into a gas volume under the atmospheric pressure (standard state) to be several mL/min. Because only such a very small amount of liquid is supplied to the vacuum, a load on the vacuum evacuation device is very small so that maintenance of the vacuum evacuation device is easy; and hence, it can be said to be practical.

In addition, because the emission tube is disposed not in the atmospheric side but in the vacuum side, a size of the droplet cluster ion that can be generated becomes large. Therefore, low damage sputtering can be performed; and hence, the depth profile analysis in the surface analysis can be more effective.

In addition, the increase in size of the droplet cluster ion also contributes to improvement of the secondary ion yield in the secondary ion mass spectrometry method.

In the present invention, the laser beam is used for heating the emission tube. If an electric heater is provided to the emission tube for preventing the freezing as a general method, the entire emission tube is unnecessarily heated so that the life of the emission tube is shortened.

Because only the distal end portion of the emission tube at which the emission opening is positioned is irradiated with the focused laser beam, the unwanted freezing can be prevented without unnecessarily heating other parts of the emission tube.

The wavelength of the laser beam may be in the range from visible light to far infrared light; namely, in the range of 0.3 μm to 10.6 μm. In particular, if the emission tube coated with gold is used, it is theoretically desired to use a far infrared (10.6 μm) beam. By using the far infrared beam, the gold-coated emission tube itself is not heated while only frozen ice can be heated. However, there is a technical difficulty in checking the irradiation position if the far infrared laser beam is used. Therefore, it is much more practical to use a visible light beam or a near infrared laser beam. In this case, the wavelength range of the laser beam is in the range of 0.3 μm to 1 μm.

First Embodiment

FIG. 1-1 illustrates an ion source 102 of the present invention.

This ion source 102 indicates the use of super large droplet cluster ions (containing a plurality of atoms and molecules in particles having charges), and includes a vacuum chamber 110 and an ionization liquid supply device 105.

An emission tube 103 is penetrated into a wall of the vacuum chamber 110. One end of the emission tube 103 is positioned outside the vacuum chamber 110; and a distal end portion 126 as the other end is positioned inside the vacuum chamber 110.

Inside the emission tube 103, a thin tube 115 is formed.

The ionization liquid supply device 105 includes a liquid storing portion 132 and a liquid feeding pump 131 connected to the liquid storing portion 132.

The thin tube 115 is connected to a liquid supply pipe 143 at a base part 136 outside the vacuum chamber 110; and the liquid supply pipe 143 is directly connected to the liquid feeding pump 131. The liquid storing portion 132 stores the ionization liquid for forming the super large droplet cluster ions. When the liquid feeding pump 131 is operated, the ionization liquid stored in the liquid storing portion 132 is supplied to the thin tube 115 in the emission tube 103.

There is hermetic sealing between the emission tube 103 and the vacuum chamber 110. A vacuum evacuation device 125 is connected to the vacuum chamber 110. When the vacuum evacuation device 125 is operated, the vacuum evacuation device 125 evacuates the inside of the vacuum chamber 110; and hence, the inside of the vacuum chamber 110 becomes vacuum environment.

The emission tube 103 has an elongated cylindrical shape, and has a constant outer diameter in a part closer to a part positioned outside the vacuum chamber 110 than the distal end portion 126.

Figures 1, 2:
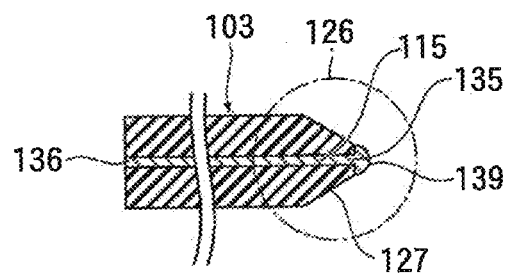
Figures 1, 2:
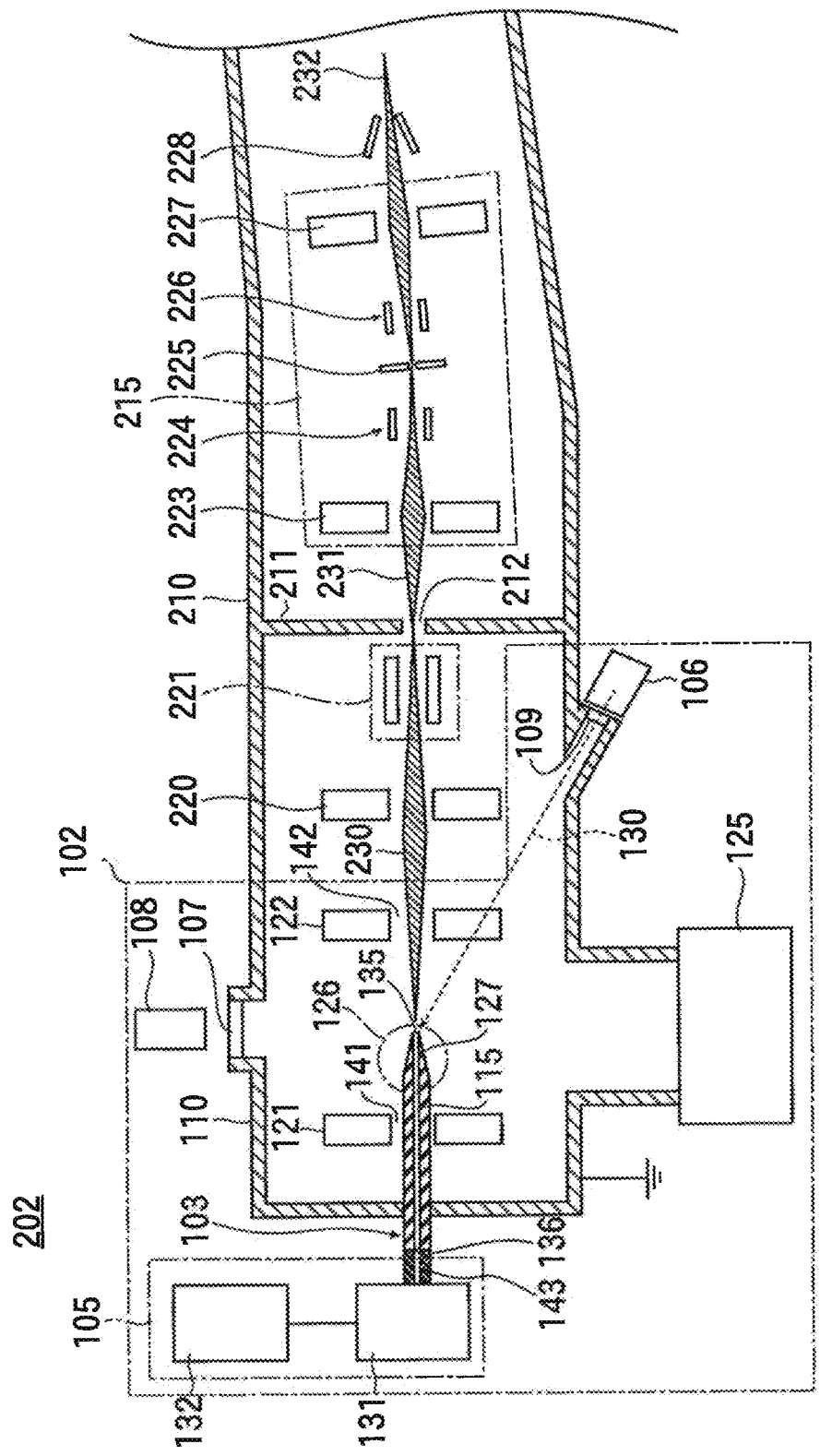
Figure 2:
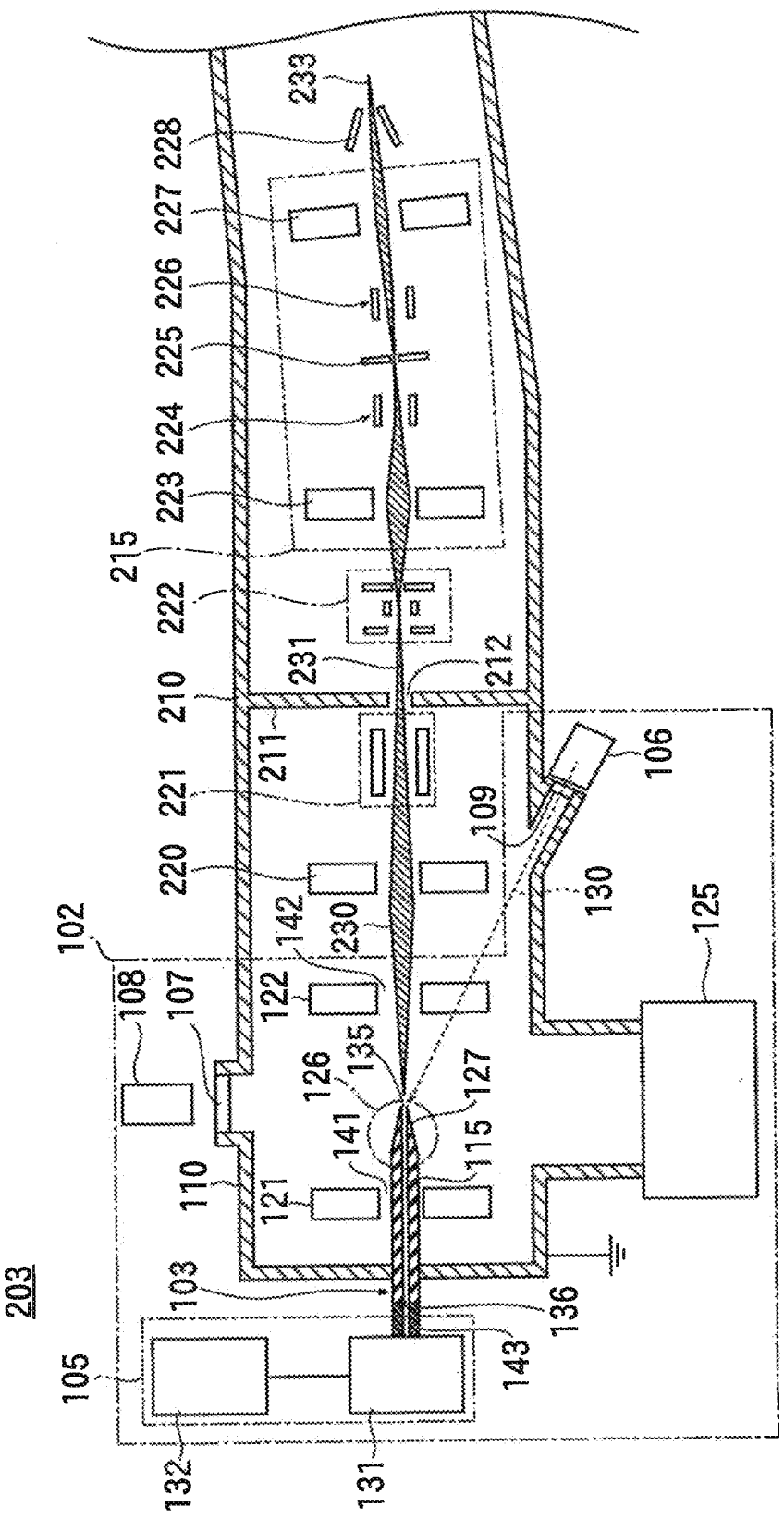

FIG. 1-2 is an enlarged diagram of the distal end portion 126.

The distal end portion 126 of the emission tube 103 is provided with an emission opening 135 connected to the thin tube 115. The thin tube 115 opens with the emission opening 135 at the distal end portion 126 of the emission tube 103.

In a part including the rim of the emission opening 135 in the distal end portion 126 of the emission tube 103, the outer diameter is gradually decreased so as to be closer to the distal end of the emission tube 103 so that a conical side surface 127 is formed in such a manner that the most distal end part forms the part around the emission opening 135.

The inside of the vacuum chamber 110 is in a vacuum environment. The ionization liquid supplied to the thin tube 115 at a position outside the vacuum chamber 110 is moved inside the thin tube 115 by a feeding pressure generated by the liquid feeding pump 131 and exits from the thin tube 115 from the emission opening 135 so as to form an expanded portion 139.

At least a surface part of the emission tube 103 surrounding the emission opening 135 is made conductive. In the ionization liquid going out of the emission opening 135, the expanded portion 139 contacts with the conductive part of the emission tube 103; and hence, the atoms and molecules contained in the expanded portion 139 end up having the same potential as the conductive part of the emission tube 103. The conductive part of the emission tube 103 and the vacuum chamber 110 are not brought into contact with each other but are electrically insulated from each other.

Here, the emission tube 103 is made of metal, but it is possible to form the emission tube 103 by forming a thin metal film on the surface of the emission tube with main body made of glass. In particular, a conductive thin film is formed on the surface of the conical side surface 127 so as to form the conductive part.

An extraction power supply 128 is disposed outside the vacuum chamber 110.

The vacuum chamber 110 is connected to the ground potential. The conductive part of the emission tube 103 is connected to the extraction power supply 128 and is applied with a voltage that is positive with respect to the ground potential.

Inside the vacuum chamber 110, there are disposed an adjustment electrode 121 connected to the extraction power supply 128 and an extracting electrode 122.

The adjustment electrode 121 is provided with an insertion hole 141; and the extracting electrode 122 is provided with an extraction hole 142. The emission tube 103 is inserted in the insertion hole 141 without contacting with the adjustment electrode 121; and the extraction hole 142 is positioned on an extension line of the thin tube 115.

In this state, the emission opening 135 is positioned between the adjustment electrode 121 and the extracting electrode 122.

The extraction power supply 128 applies, to the adjustment electrode 121, a high voltage that is positive or negative with respect to the conductive part of the emission tube 103, and applies, to the extracting electrode 122, a high voltage that is negative with respect to the conductive part of the emission tube 103.

In the ionization liquid brought into contact with the conductive part of the emission tube 103, molecule ions having positive charge generated by dissociation have the same potential as the conductive part of the emission tube 103 and are therefore extracted in the direction toward the distal end side by the electric field formed in a vicinity of the distal end portion 126 of the emission tube 103 by the extracting electrode 122 and the adjustment electrode 121. Because the molecule ions having positive charge are gathered to the distal end portion 126 of the emission tube 103, the expanding portion 139 is formed. The expanded portion 139 keeps its shape by surface tension of the ionization liquid. Because the molecule ions having positive charge are gathered, Coulomb repulsion force is generated between the ions having positive charge. When the surface tension of the ionization liquid in the distal end portion 126 becomes unable to suppress the Coulomb repulsion force, a droplet cluster ion including a plurality of atoms is generated and is accelerated in the direction where the extracting electrode 122 is positioned.

The droplet cluster ions generated in this way pass through the extraction hole 142 formed in the extracting electrode 122 and is emitted as a droplet cluster ion beam 145.

Consequently, when the expanded portion 139 is formed by the electric field at the distal end portion 126 of the emission tube 103 so that the portion is exposed to the vacuum environment, a part of the molecule ions in the ionization liquid positioned at the emission opening 135 is vaporized so that evaporation heat is lost; and hence, the ionization liquid at the part of the emission opening 135 is cooled. Then, the part that becomes a freezing temperature of the ionization liquid or lower is frozen. The ionization liquid frozen in the vicinity of the emission opening 135 blocks the emission opening 135; and hence, the ionization liquid cannot go out of the emission opening 135.

This vacuum chamber 110 is provided with an irradiation window 109; and a laser beam emitting device 106 is disposed at a position close to the irradiation window 109 outside the vacuum chamber 110. The irradiation window 109 is transparent to the laser beam emitted by the laser beam emitting device 106; and the emitted laser beam passes through the irradiation window 109 so as to go from the outside to the inside of the vacuum chamber 110. Reference numeral 130 in FIG. 1-1 refers to an optical axis of the laser beam.

A direction of the laser beam emitting device 106 is adjusted so that the emitted laser beam irradiates the surface of the emission tube 103 at the distal end portion, particularly the conical side surface 127 including the emission opening 135. When the charged particles are emitted, the laser beam irradiates the part of the emission tube 103 including the emission opening 135 so that the part irradiated with the laser beam is heated. Consequently, the temperature of the part irradiated with the laser beam and the surrounding part is raised so that the temperature of the ionization liquid positioned inside the emission tube 103 does not reach freezing temperature or lower.

Therefore, the thin tube 115 is not blocked with the frozen ionization liquid and can continue to emit charged particles.

This vacuum chamber 110 is provided with an observation window 107 formed in the wall so that the emission opening 135 and its vicinity can be observed through the observation window 107. The laser beam emitting device 106 is provided with an emission direction changing device so that the emission direction of the laser beam can be changed.

While the laser beam is emitted from the laser beam emitting device 106 so as to irradiate the distal end portion 126 of the emission tube 103, the distal end portion 126 of the emission tube 103 is observed through the observation window 107, and the emission direction changing device is operated. Thus, the direction of the emitted laser beam can be changed so that the entire rim of the emission opening 135 and the distal end of the conical side surface 127 are irradiated with the laser beam.

The laser beam irradiates the surface of the conical side surface 127 including the rim part of the emission opening 135 but does not irradiate the part having constant diameter of the emission tube 103. Then, it is possible to minimize the damage to the emission tube 103 due to laser irradiation.

An optical microscope 108 is disposed in a vicinity of the observation window 107 outside the vacuum chamber 110. When changing the direction of the laser beam, the emission opening 135 of the emission tube 103 and its vicinity may be observed by the optical microscope 108 while irradiating the distal end portion 126 of the emission tube 103 with the laser beam from the laser beam emitting device 106.

In addition, instead of the optical microscope 108, an optical detection device may be disposed so as to detect by the optical detection device that the laser beam irradiates the emission opening 135 and its vicinity.

Further, in the embodiment described above, stainless steel is used as a capillary material for forming the emission tube 103, and the diameter of the thin tube 115 and the outer diameter of the emission tube 103 are approximately 40 μm and approximately 200 μm, respectively.

As the ionization liquid, a trifluoroacetic acid solution is stored in the liquid storing portion 132, and the liquid feeding pump 131 supplies the solution to the emission tube 103 at a flow rate of approximately 0.5 mL/min to approximately 10 μL/min. Further, if a vapor of the trifluoroacetic acid is exposed to arcing, active fluorine atoms may be generated and intensely react with the metal surface so that an insulative film is formed afterward. If the influence cannot be ignored, acetic acid may be used as the ionization liquid.

A high voltage in the range of approximately +1 kV to approximately +30 kV (or higher) with respect to the ground potential may be applied to the conductive part of the emission tube 103.

The extracting electrode 122 is disposed on a center axis that passes the center of the emission opening 135 and is perpendicular to the plane on which the emission opening 135 is positioned at a position apart from the emission opening 135 positioned at the distal end of the emission tube 103 by approximately 1 mm or more to approximately 5 mm or less. The extraction hole 142 formed in the extracting electrode 122 is a circular hole with the center at an intersection with the center axis and a diameter of approximately 3 mm.

This extracting electrode 122 is applied with a voltage of approximately −2 kV with respect to the conductive part of the emission tube 103.

As the laser beam for preventing freezing, a near infrared laser having a wavelength of 808 nm is used, and the laser beam having a power of approximately 0.1 W is condensed on the emission tube 103 to be approximately ϕ500 μm.

It is preferred that the laser beam enter the emission opening 135 in a direction as close as possible to the orthogonal direction from the front side, but it is practical to make the laser beam enter the emission opening 135 at an angle of 20° or larger to 80° or smaller.

In addition, the adjustment electrode 121 is disposed at a position opposite to the extracting electrode 122 with respect to the emission opening 135. In order to adjust the electric field in a vicinity of the emission opening 135, the adjustment electrode 121 is applied with a voltage in the range of approximately −3 kV to approximately +3 kV with respect to the conductive part of the emission tube 103.

Second Embodiment

Next, in reference to FIG. 2-1, an ion gun 202 using the above-discussed ion source 102 is described.

This ion gun 202 is an ion gun for sputtering of a sample surface. A first transport lens electrode 220 and a Wien filter 221 are disposed behind the extracting electrode 122 of the ion source 102. A super large droplet cluster ion beam 230 that has passed through the extracting electrode 122 enters the first transport lens electrode 220 and is focused so that the cluster ion beam can effectively pass through an opening 212 in a partition plate 211 disposed on the downstream side. Next, the cluster ion beam enters the Wien filter 221 and undergoes mass separation so as to be droplet cluster ions having a desired cluster size.

The partition plate 211 having the opening 212 is disposed on the downstream side of the Wien filter 221. The droplet cluster ions that have passed through the Wien filter 221 irradiate the partition plate 211, and droplet cluster ions 231 selected to have a desired cluster size pass through the opening 212 and enter the inside of a barrel chamber 210.

A focusing device 215 is disposed inside the barrel chamber 210.

In this case, the focusing device 215 includes a second transport lens electrode 223, a bend deflection electrode 224, a aperture 225, a raster deflection electrode 226, and an objective lens electrode 227, which are disposed in this order from the opening 212 side. The droplet cluster ions 231 entering the barrel chamber 210 pass through those electrodes so as to be focused and deflected, pass through an ion gun distal end ground electrode 228 disposed on the downstream side of the objective lens electrode 227, and are emitted as a cluster ion beam 232 from the ion gun 202. Further, the electrodes from the bend deflection electrode 224 to the downstream side are disposed on a center axis bent from a center point of the bend deflection electrode 224 by approximately 2 degrees or more to approximately 10 degrees or less. With this layout, electrically neutral molecules are removed from the ion beam.

FIG. 2-2 illustrates an ion gun 203 that can emit the cluster ion beam as a pulse beam. Because a beam pulse electrode 222 is disposed at a position inside the barrel chamber 210 on the upstream side of the second transport lens electrode 223, a continuous ion beam, as well as a pulse cluster ion beam, can be generated. The cluster ion 231 that has passed through the opening 212 becomes like a pulse when passing through the beam pulse electrode 222. The cluster ions flying like a pulse enter the focusing device 215 to be focused and deflected, and then pass through the ion gun distal end ground electrode 228 to be a pulse-like cluster ion beam 233, which is emitted from the barrel chamber 210.

This ion gun 203 not only has a function of performing sputtering of the sample surface by a continuous beam similar to the ion gun 202, but can also irradiate the sample surface with the pulse beam. Therefore, the ion gun 203 can be used for sample surface sputtering by the pulse beam and can be used as a pulse beam primary ion gun in the secondary ion mass spectroscopy (SIMS).

In the ion source 102 disposed in the ion guns 202 and 203 described above and the ion source 102 disposed in each analysis instrument described later, the laser beam irradiates the emission opening 135. Therefore, the emission opening 135 is not blocked by freezing of the ionization liquid; and emission of the cluster ion beam 232 or 233 is not stopped.

Further, when the cluster ion beam 232 is emitted, the inside of the vacuum chamber 110 and the inside of the barrel chamber 210 are in a vacuum environment.

Third Embodiment

Figure 3:
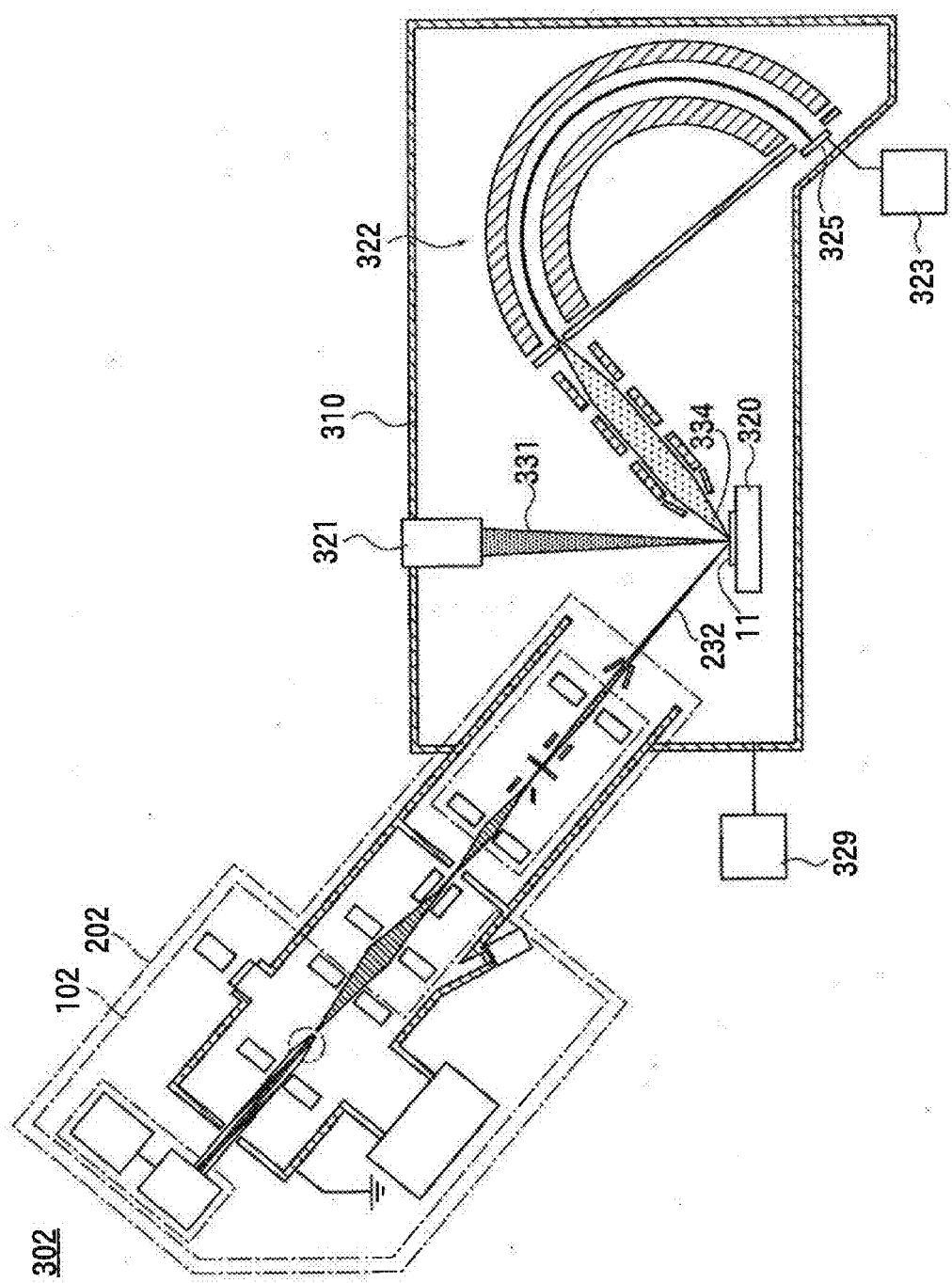
FIG. 3 illustrates an X-ray photoelectron spectroscopy instrument (XPS).

FIG. 3 illustrates an analysis instrument 302 of the present invention, which is an X-ray photoelectron spectroscopy analysis instrument (XPS) including the above-discussed ion gun 202 so as to perform the X-ray photoelectron spectroscopy using the cluster ion beam.

This analysis instrument includes an analysis chamber 310, to which a vacuum pump 329 is connected and which is evacuated by the vacuum pump 329; hence, the inside of the analysis chamber 310 is the vacuum environment. Further, the inside of the ion gun 202 is also in a vacuum environment.

A sample stage portion 320 is disposed inside the analysis chamber 310; and a sample 11 placed on the sample stage portion 320 in the vacuum environment is irradiated with the cluster ion beam 232 emitted from the ion gun 202.

An X-ray emitting device 321 that emits a soft X-ray (such as Al—Kα or Mg—Kα) 331 is disposed at a position facing the sample stage portion 320. A position of the sample 11 irradiated with the cluster ion beam 232 is also irradiated with the soft X-ray 331 emitted from the X-ray emitting device 321.

When the surface of the sample 11 is irradiated with the soft X-ray 331, electrons are emitted from the irradiated part by photoelectric effect.

Inside the analysis chamber 310, there is disposed an electron spectrometer 322. When electrons 334 having a desired set energy emitted from the sample 11 pass through the electron spectrometer 322, the electrons 334 are analyzed by the electron spectrometer 322 and are detected by a detector 325.

A calculator 323, connected to the detector 325, which determines detection intensity corresponding to energy of the electrons from a result of the detection; and a type and a state of valence of atoms on the surface of the sample 11 are determined.

After the data are determined, an analyzed part of the sample 11 is irradiated with the cluster ion beam 232 by the ion gun 202. Then, the surface of the sample 11 is exfoliated so that a new surface of the sample 11 is exposed. By irradiating the part with the soft X-ray 331, the depth profile analysis can be performed.

Fourth Embodiment

Figure 4:
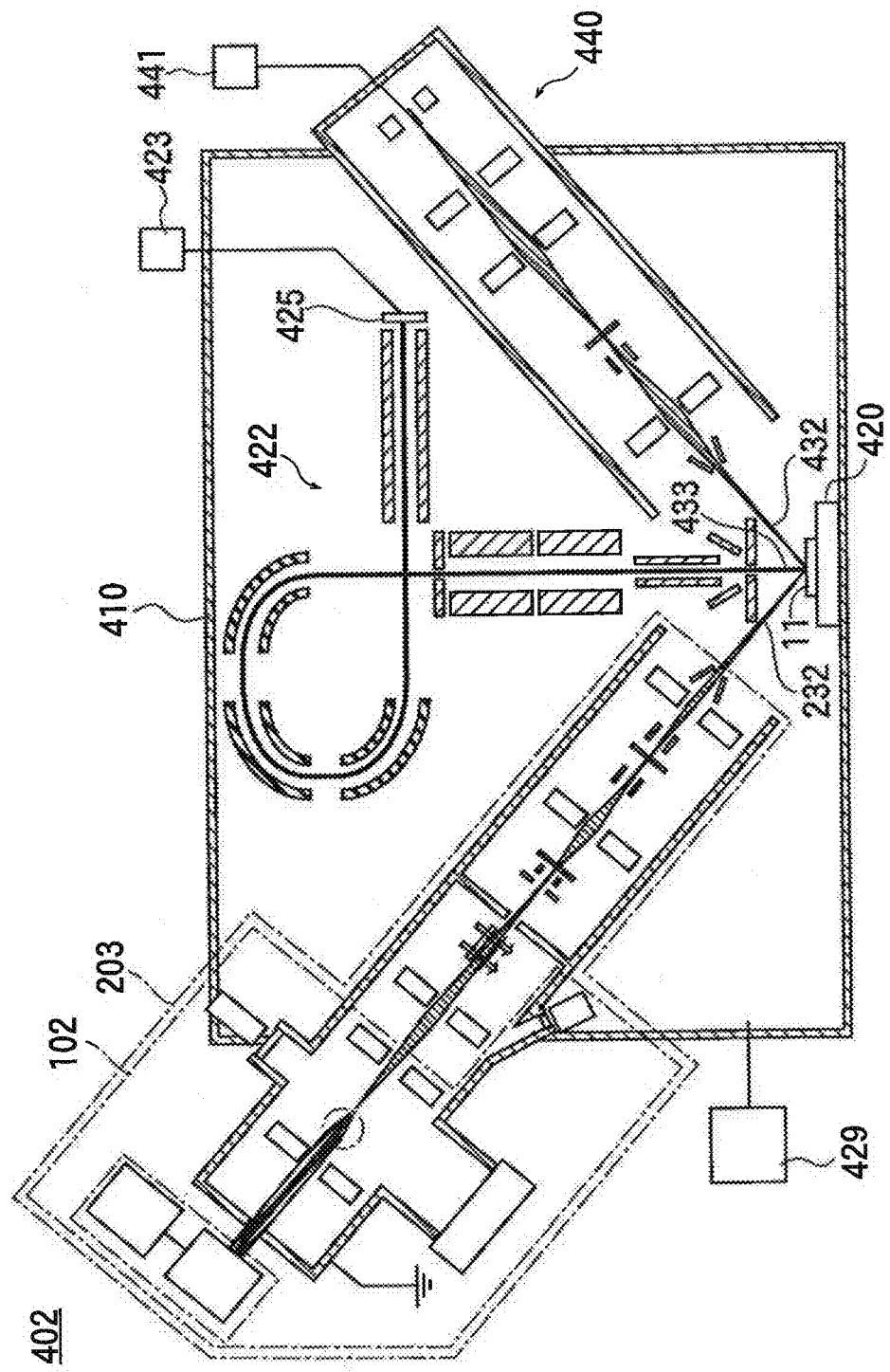
FIG. 4 illustrates a secondary ion mass spectroscopy instrument (SIMS).
Figure 5:
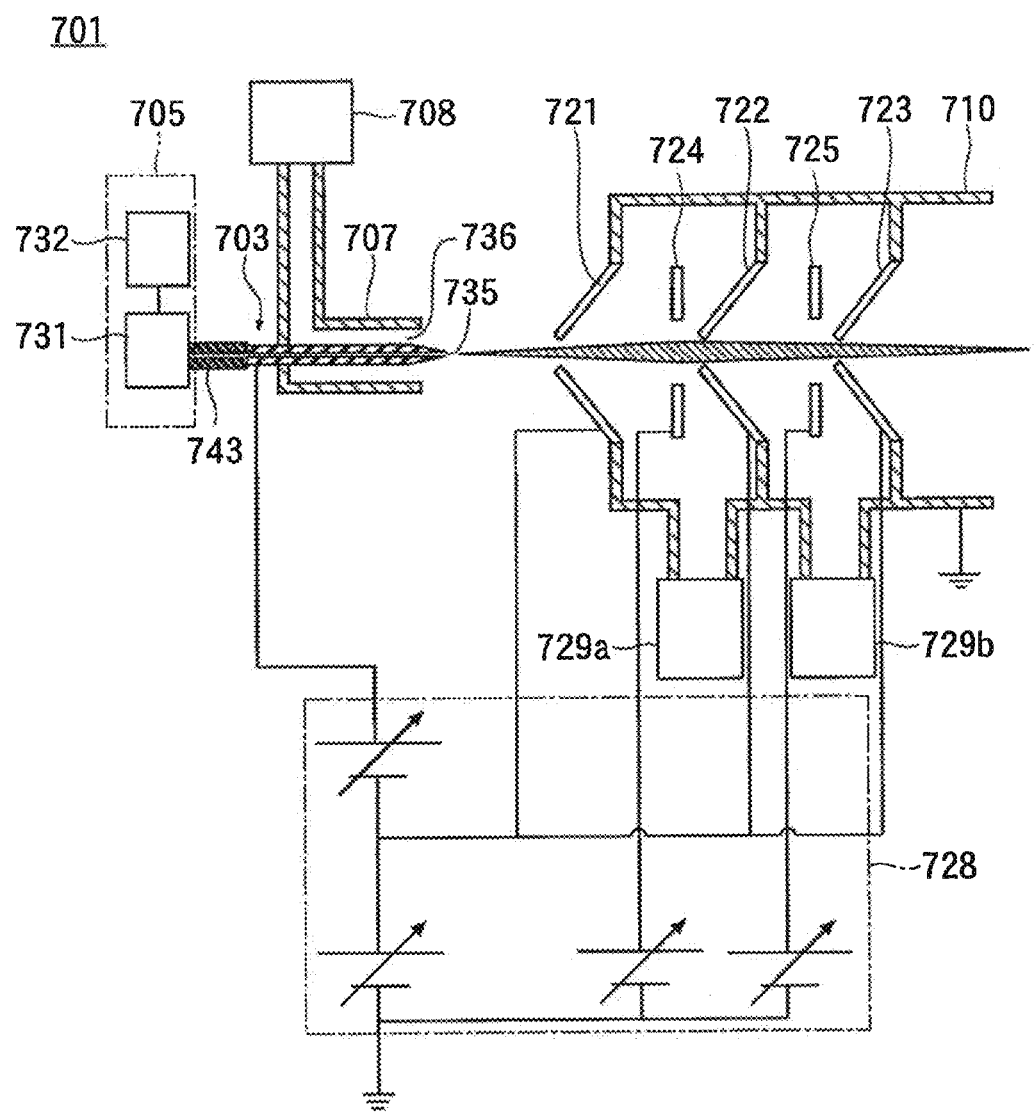
FIG. 5 illustrates a typical atmospheric charged droplet ion source.

FIG. 4 illustrates an analysis apparatus 402 (TOF-SIMS) of the present invention, which includes the ion gun 203 that can emit not only the continuous beam but also the pulse cluster ion beam 232, and a metal ion gun 440 that generates an ion beam from a liquid metal ion source 441 to emit a primary ion beam 432 constituted of a pulse-like metal ion beam.

A sample stage portion 420 is disposed inside an analysis chamber 410, and the sample 11 is placed on the sample stage portion 420.

The pulse-like cluster ion beam 232 and the pulse-like primary ion beam 432 emitted from the ion guns 203 and 440 irradiate the same place on the sample 11. Examples of metal ions for use by the primary ion beam 432 include $Ga^+$, $Au^+$, $Bi^+$, $Au_3^{++}$, and $Bi_3^{++}$.

The analysis chamber 410 is vacuum evacuated by a vacuum evacuation device. When the sample 11 is irradiated with the cluster ion beam 232 and the primary ion beam 432, substances forming the sample 11 are exfoliated from the surface of the sample 11 by the ion sputtering, and a part of the substances becomes secondary ion particles 433 and are emitted from the surface of the sample 11.

Inside the analysis chamber 410, there is disposed a time-of-flight secondary ion mass spectroscopy instrument 422. The incident secondary ion particles are analyzed in accordance with a mass-to-charge ratio (m/z) and enter a detection device 425 so that detection intensity corresponding to the mass-to-charge ratio is determined by a calculator 423.

As methods of irradiation using the cluster ion beam 232 and the primary ion beam 432, there are the following methods of irradiation: (a) perform sputtering by irradiating with the cluster ion beam 232 so as to perform the depth profile analysis with low damage, (b) irradiate with the primary ion beam 432 after irradiation with the cluster ion beam 232 so as to increase generation amount of secondary ion particles by the primary ion beam 432 and to improve detection sensitivity, and (c) perform both (a) and (b) so as to perform the depth profile analysis with low damage and high sensitivity.

Further, in the analysis instrument 302 and 402 described above, X-ray detection is not performed. However, also when the surface of the sample 11 is irradiated with an electron beam or an X-ray so that the emitted characteristic X-ray or fluorescent X-ray is analyzed, it is possible to use the ion gun 202 or 203 so as to sputter-remove the surface of the sample 11 for performing the depth profile analysis. In addition, also when performing Auger analysis by emitting Auger electrons, it is possible to use the ion gun 202 or 203 so as to sputter-remove the surface of the sample 11 for performing the depth profile analysis.

Fifth Embodiment

Figure 6:
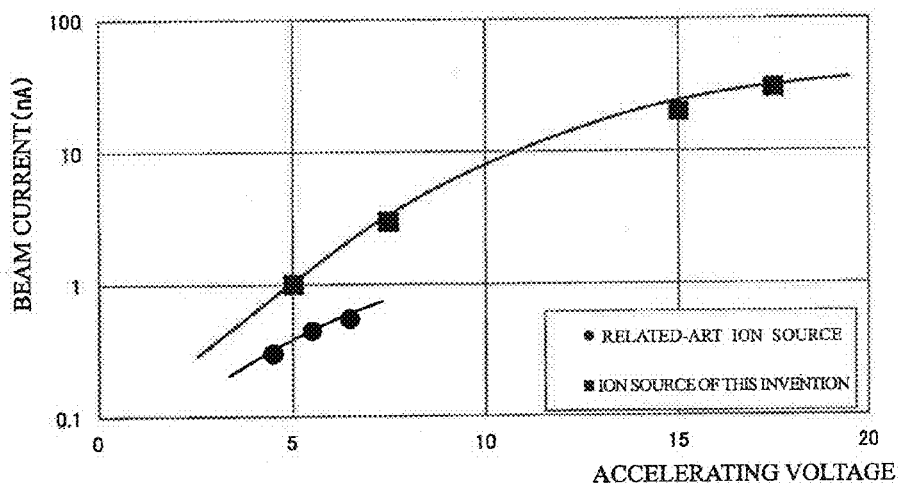
FIG. 6 is a graph showing a comparison of obtainable maximum current.

FIG. 6 is a graph showing a relationship between a value of a voltage applied to the conductive part of the emission tube 103 of the ion source 102 of the present invention as the accelerating voltage with respect to the ground voltage (a horizontal axis indicates the accelerating voltage) and a current value of the droplet cluster ion beam (a vertical axis indicates the beam current). FIG. 6 shows that even if the accelerating voltage is the same, when the current value of the cluster ion beam formed by the ion source of the present invention is larger, then the ion source 102 of the present invention can be applied with a higher voltage than that of the related-art ion source.

Figure 7:
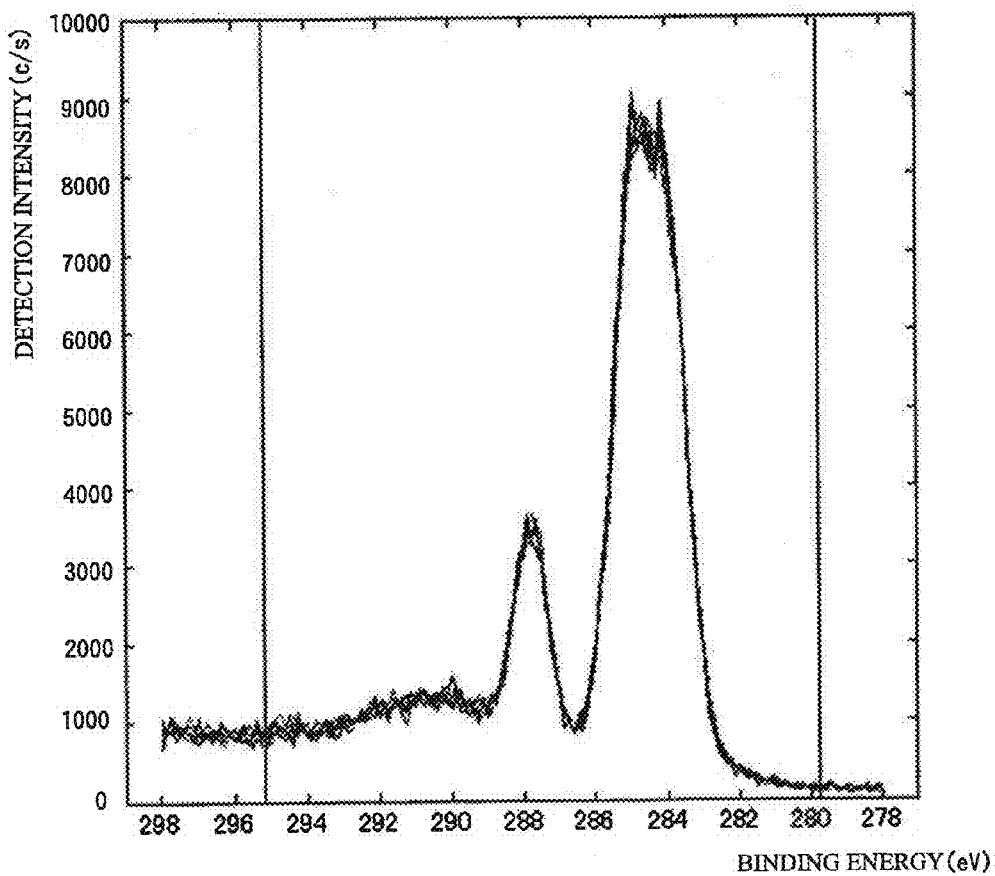
FIG. 7 is a graph showing a low damage example of an organic polymer material in the X-ray photoelectron spectroscopy by ion source sputtering of the present invention.

FIG. 7 is a graph when a sample made of polyimide is irradiated and sputtered by the cluster ion beam from the ion gun of the present invention with an accelerating voltage of 15 kV and a beam current of 10 nA, and then the X-ray photoelectron spectroscopy analysis (XPS) is performed. The horizontal axis indicates binding energy, and the vertical axis indicates detection intensity (measured number/second). The irradiation with the cluster ion beam is performed to grind the sample surface; and the analysis is performed a plurality of times so as to superimpose the graphs indicating the spectrum. It is understood that there is no change in the shape of the spectrum even the irradiation is continued.

Figure 8:
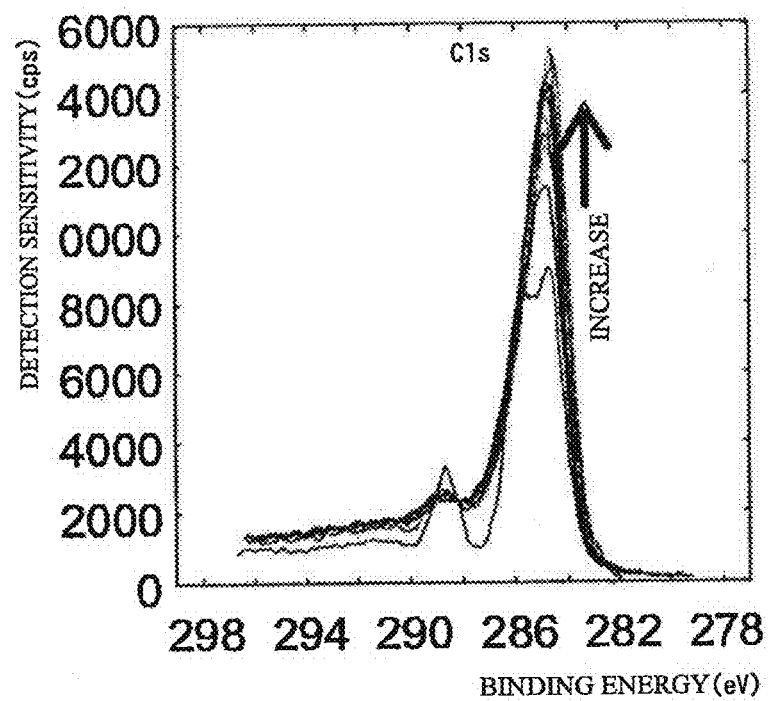
FIG. 8 is a graph showing a damage generation example of the organic polymer material in the X-ray photoelectron spectroscopy by $C_{60}$ ion source sputtering.

FIG. 8 shows a result of superposed graphs indicating the spectrum when grinding of the sample made of polyimide by irradiation with a fullerene ($C_{60}$) ion beam with an accelerating voltage of 10 kV and C1s XPS spectrum analysis were repeatedly performed.

When using the fullerene, damage occurs due to sputtering or deposition of fullerene ions on the sample surface so that stable sputtering is not performed, and the graphs do not match with each other. Therefore, it is understood that the fullerene ion beam irradiation is not suitable for the depth profile analysis.

Figures 1, 9:
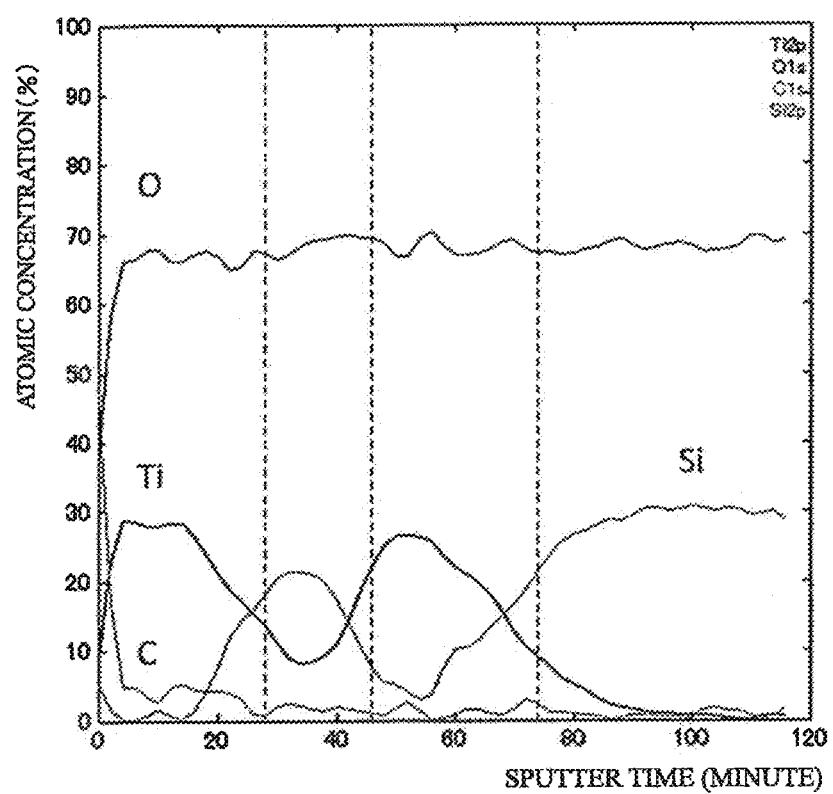
Figures 2, 9:
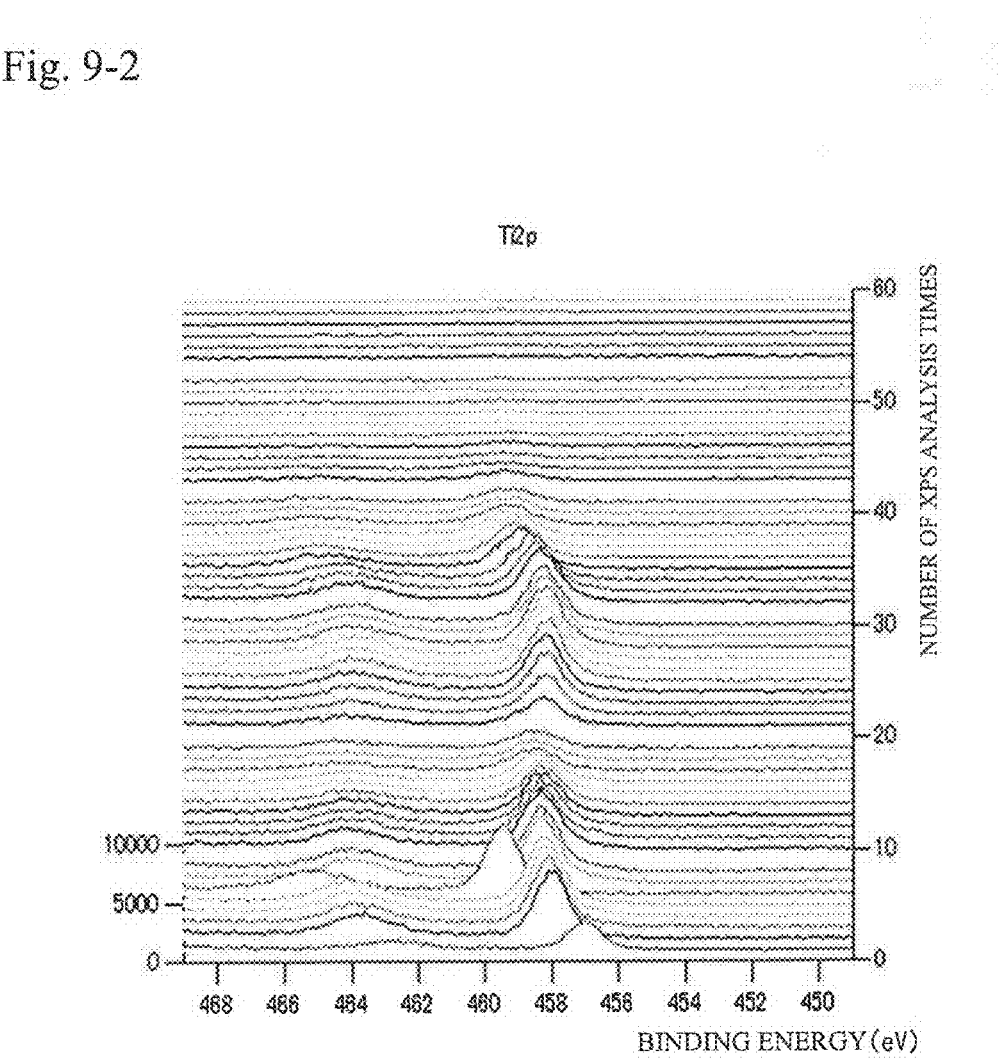

FIG. 9-1 and FIG. 9-2 show results of the depth profile analysis in which a thin film having three-layered structure of $TiO_2$ (25 nm)/$SiO_2$ (25 nm)/$TiO_2$ (25 nm) was formed on a substrate that $SiO_2$ was exposed on the surface, and irradiation with the cluster ion beam having an accelerating voltage of 15 kV and a beam current of 10 nA from the ion gun of the present invention and the XPS analysis were repeatedly performed. FIG. 9-1 is a graph showing a relationship between a sputter time (the horizontal axis) and atomic concentration of individual atoms. FIG. 9-2 is a graph showing a relationship among binding energy of titanium peak (Ti 2p3/2) (the horizontal axis), measured intensity (a virtual axis in the height direction), and the number of analysis times (the vertical axis).

As understood from FIG. 9-1, an increase or decrease state of atoms is so clear that an interface between layers of the three-layered thin film can be specified, and it is understood from FIG. 9-2 that there is almost no change in the shape of the spectrum.

Figures 1, 10:
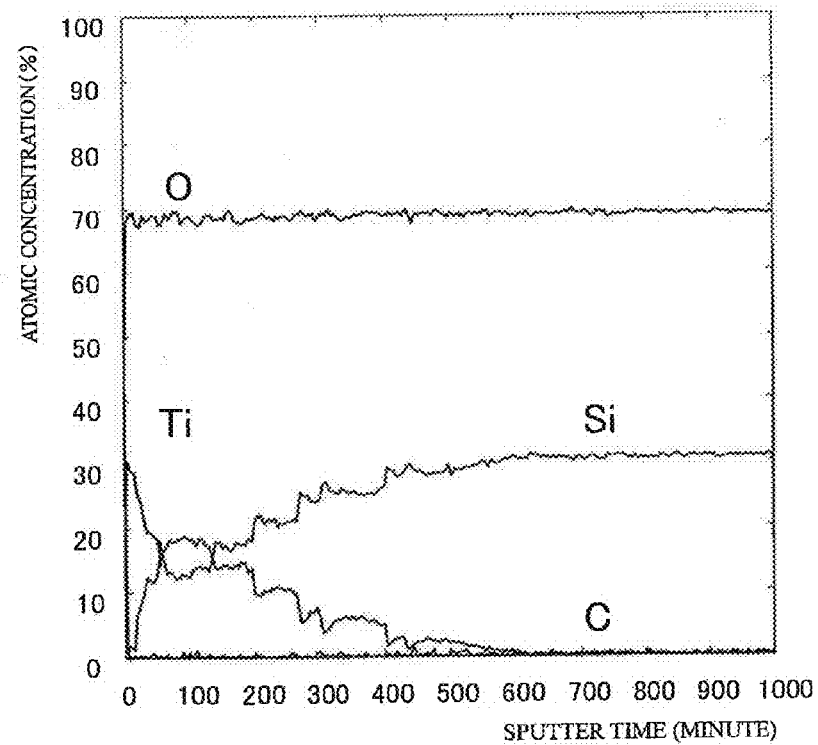
Figures 2, 10:
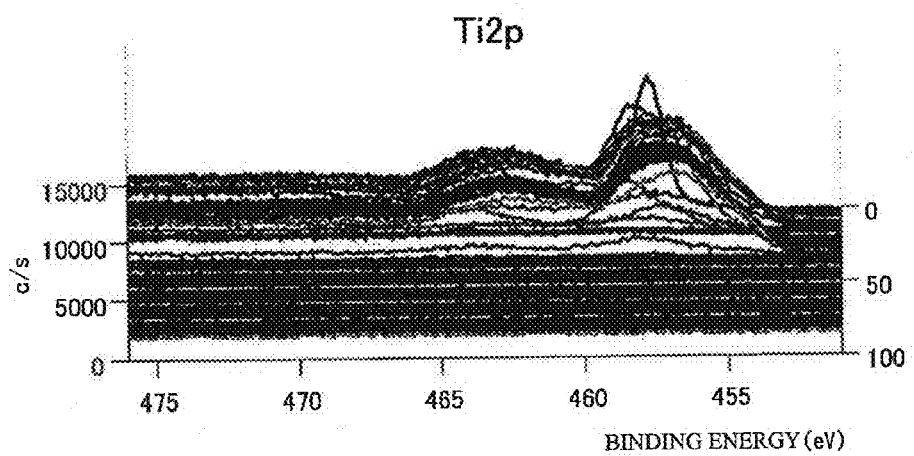

On the sample having the same composition, irradiation with an argon cluster ion beam (Ar-GCIB) having an accelerating voltage of 20 kV and the XPS analysis were repeatedly performed. A result of the measurement is shown in FIG. 10-1 and FIG. 10-2. In FIG. 10-1, concentration variation of the graph indicating atomic concentration is not clear; and hence, the interface cannot be specified. In FIG. 10-2, the shape of the spectrum is significantly different from expected one.

Next, a sample made of copper foil was irradiated with the ion cluster beam having an accelerating voltage of 15 kV and a beam current of 7 nA from the ion gun of the present invention; and before and after the irradiation, the sample was irradiated with a primary beam constituted of a $Bi^+$ metal ion beam having an accelerating voltage of 30 kV so that sputtered particles were analyzed (TOF-SIMS analysis).

Figures 1, 11:
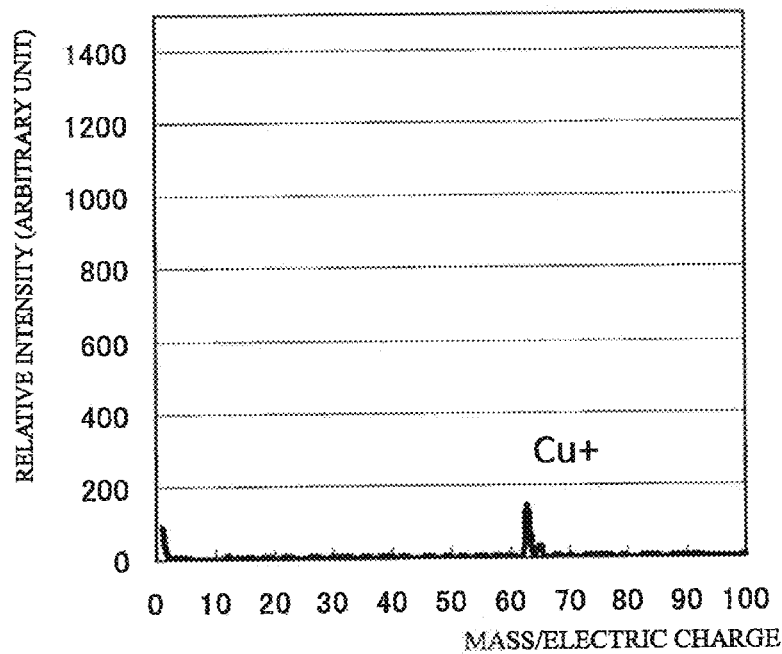
Figures 2, 11:
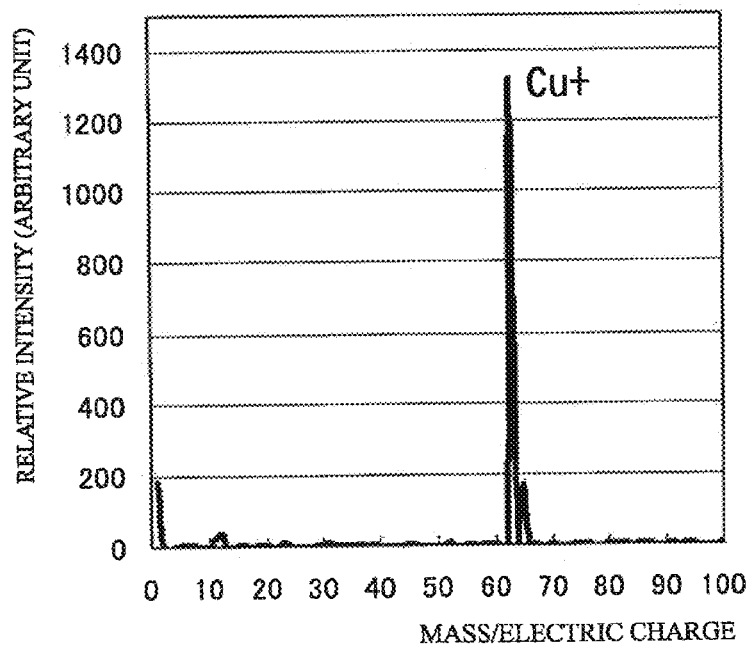

FIG. 11-1 shows an analysis result before the irradiation; and FIG. 11-2 shows an analysis result just after the irradiation with the primary ion beam for 10 minutes. The horizontal axis indicates the mass-to-charge ratio; and the vertical axis indicates relative intensity. Peaks of $Cu^+$ are at the same position with the same height, but the number of detection times of $Cu^+$ after irradiation with the cluster ion beam is seven times the number of detection times before the irradiation; and hence, sensitivity is improved seven fold.

Next, a sample made of PMMA as an organic substance was irradiated with the cluster ion beam having an accelerating voltage of 15 kV and a beam current of 8 nA from the ion gun of the present invention; and then the sample was irradiated with a $Bi_3^{++}$ primary ion beam of 30 kV while the time-of-flight secondary ion mass spectrometry (TOF-SIMS) was performed.

Figures 1, 12:
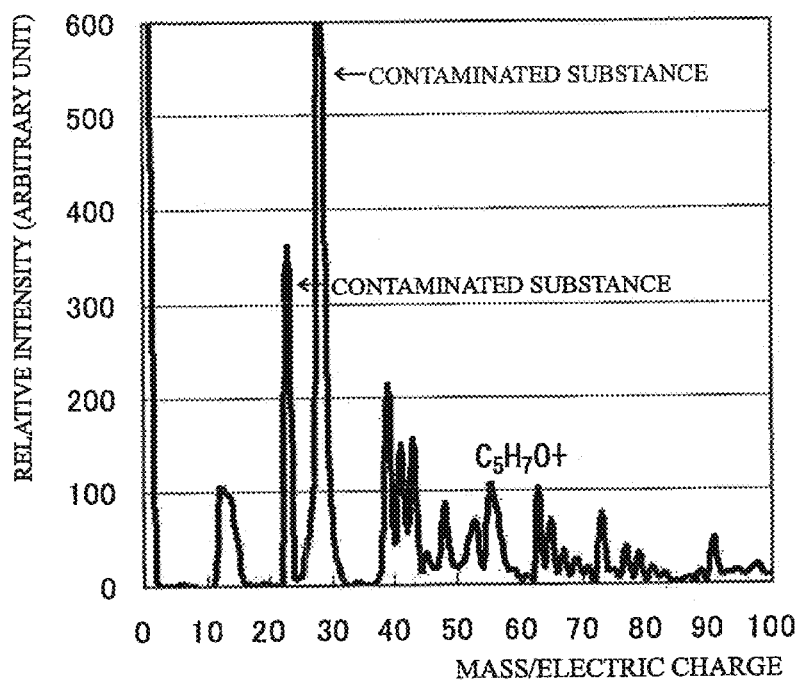
Figures 2, 12:
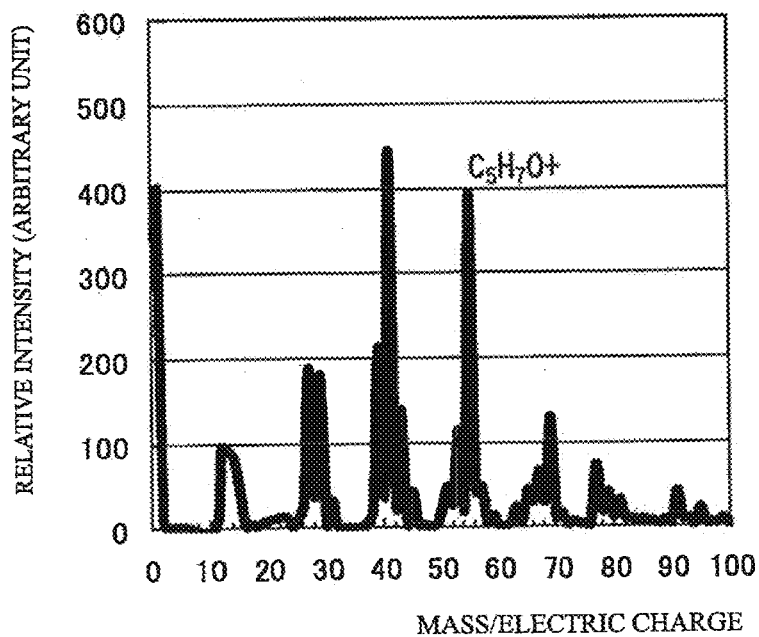

FIG. 12-1 shows an analysis result before the irradiation; and FIG. 12-2 shows an analysis result just after the irradiation. The scale of the vertical axis of FIG. 12-2 indicates measured values of four times the scale of the vertical axis of FIG. 12-1; and the detection sensitivity is increased. In addition, it is understood that the detection sensitivity is improved by the action of irradiation with the cluster ion beam.

Further, it is known that the detection sensitivity is increased when the TOF-SIMS analysis is performed while blowing oxygen gas directly to the sample. However, as a side effect of this method, sputtering speed becomes very slow when the depth profile analysis is performed using a combination of many types of sputtering ion guns.

In the case of irradiation with the cluster ion beam of the present invention as this example, the problem of slow sputtering speed does not occur. Therefore, in the case of the depth profile analysis using together the super large droplet cluster ion beam, both effects of the low damage sputtering and the improvement of sensitivity are obtained at the same time. Therefore, the depth profile analysis in the TOF-SIMS using the pulse beam ion gun of the present invention is useful in both views of sensitivity and low damage.

Also in the case of the TOF-SIMS analysis using the pulse beam ion gun of the present invention as the primary ion beam, the sensitivity increasing effect can be directly expected. Further, also in the depth profile analysis in which the cluster ion beam is used as both the primary ion beam for TOF-SIMS and the sputtering ion gun, the advantages or benefits of the low damage sputtering and the sensitivity increasing effects can be obtained.

What is claimed is:

1. An ion source, comprising:
   a vacuum chamber;
   an emission tube inserted in the vacuum chamber in a hermetic manner, the emission tube having conductivity in at least a surface thereof;
   an ionization liquid supply device disposed outside the vacuum chamber so as to supply ionization liquid to a thin tube disposed in the emission tube, at a part positioned outside the vacuum chamber;
   an extracting electrode configured to extract ions in the ionization liquid supplied from the ionization liquid supply device to the emission tube, as cluster ions from an emission opening of the thin tube positioned inside the vacuum chamber and to cause the cluster ions to travel in vacuum environment, the cluster ions being generated when surface tension of the ionization liquid at the emission opening of the thin tube is unable to suppress the Coulomb repulsion force of the ions of the same charge; and
   a laser beam emitting device configured to irradiate the emission opening with a laser beam.

2. An ion source according to claim 1, wherein a transparent window for observation of the emission opening is provided on the vacuum chamber, and wherein the vacuum chamber is configured to be able to observe the emission opening through the transparent window for observation.

3. An ion source according to claim 2, further comprising a measurement device disposed outside the vacuum chamber for observing the emission opening and for checking whether or not the emission opening is irradiated with the laser beam.

4. An ion source according to claim 2, further comprising an optical microscope for observing the emission opening, the optical microscope being disposed outside the vacuum chamber.

5. An ion source according to claim 1, wherein the laser beam emitting device emits the laser beam having a wavelength in a range of from $0.3\times10^{-6}$ m to $1\times10^{-6}$ m.

6. An ion source according to claim 1, wherein the ionization liquid contains at least one type of solvent selected from the group consisting of water, alcohol, acetonitrile, acetic acid, and trifluoroacetic acid.

7. An ion gun for emitting a cluster ion beam, comprising:
a ion source and
a focusing device configured to focus and deflect a flow of the traveling cluster ions so as to generate the cluster ion beam;
the ion source including:
a vacuum chamber;
an emission tube inserted in the vacuum chamber in a hermetic manner, the emission tube having conductivity in at least a surface thereof;
an ionization liquid supply device disposed outside the vacuum chamber so as to supply ionization liquid to a thin tube disposed in the emission tube, at a part positioned outside the vacuum chamber;
an extracting electrode configured to extract ions in the ionization liquid supplied from the ionization liquid supply device to the emission tube, as cluster ions from an emission opening of the thin tube positioned inside the vacuum chamber and to cause the cluster ions to travel in vacuum environment, the cluster ions being generated when surface tension of the ionization liquid at the emission opening of the thin tube is unable to suppress the Coulomb repulsion force of the ions of the same charge; and
a laser beam emitting device configured to irradiate the emission opening with a laser beam.

8. An analysis instrument for analyzing a surface of a sample, comprising:
an ion gun for emitting a cluster ion beam; and
a sample stage portion on which the sample is placed and the sample is irradiated with the cluster ion beam,
the ion gun including:
an ion source; and
a focusing device configured to focus and deflect a flow of the traveling cluster ions so as to generate the cluster ion beam;
the ion source including:
a vacuum chamber;
an emission tube inserted in the vacuum chamber in a hermetic manner, the emission tube having conductivity in at least a surface thereof;
an ionization liquid supply device disposed outside the vacuum chamber so as to supply ionization liquid to a thin tube disposed in the emission tube, at a part positioned outside the vacuum chamber;
an extracting electrode configured to extract ions in the ionization liquid supplied from the ionization liquid supply device to the emission tube, as cluster ions from an emission opening of the thin tube positioned inside the vacuum chamber and to cause the cluster ions to travel in vacuum environment, the cluster ions being generated when surface tension of the ionization liquid at the emission opening of the thin tube is unable to suppress the Coulomb repulsion force of the ions of the same charge; and
a laser beam emitting device configured to irradiate the emission opening with a laser beam.

9. An analysis instrument according to claim 8, further comprising:
a mass spectrometer configured to pass through secondary ions having a desired mass-to-charge ratio among secondary ions emitted from a part of the sample irradiated with the cluster ions;
a detector configured to detect the secondary ions that have passed through the mass spectrometer; and
a data processor configured to determine an amount of the secondary ions for each mass of the secondary ions based on a result of detection by the detector.

10. An analysis instrument according to claim 8, further comprising a metal ion gun configured to irradiate the sample with a primary beam of metal ions.

11. An analysis instrument according to claim 8, further comprising:
an X-ray emitting device configured to emit an X-ray to irradiate the surface of the sample irradiated with the cluster ions;
an electron spectrometer configured to pass through electrons having desired energy among electrons emitted from a part of the sample irradiated with the X-ray; and
an electron detector configured to detect the electrons that have passed through the electron spectrometer.

* * * * *